(12) United States Patent
Frye

(10) Patent No.: US 6,393,846 B1
(45) Date of Patent: May 28, 2002

(54) MANIFOLD FOR USE IN A PORTABLE LIQUID OXYGEN UNIT

(75) Inventor: Mark Robert Frye, Bloomington, IN (US)

(73) Assignee: Mallinckrodt Inc., St. Louis, MO (US)

(*) Notice: Subject to any disclaimer, the term of this patent is extended or adjusted under 35 U.S.C. 154(b) by 0 days.

(21) Appl. No.: 09/696,219

(22) Filed: Oct. 26, 2000

Related U.S. Application Data

(60) Provisional application No. 60/162,132, filed on Oct. 29, 1999.

(51) Int. Cl.$^7$ ................................................ F17C 13/00
(52) U.S. Cl. ........................................ 62/50.5; 62/50.7
(58) Field of Search .................................. 62/50.7, 50.5

(56) References Cited

U.S. PATENT DOCUMENTS

| | | | |
|---|---|---|---|
| 3,433,028 A | * 3/1969 | Klee | ............................ 62/50.7 |
| 3,864,928 A | 2/1975 | Eigenbrod | |
| 4,211,086 A | 7/1980 | Leonard et al. | |
| 4,745,760 A | * 5/1988 | Porter | ......................... 62/50.7 |
| 4,887,433 A | * 12/1989 | Locatelli | ...................... 62/50.7 |
| 5,357,758 A | 10/1994 | Andonian | |
| 5,417,073 A | 5/1995 | James et al. | |
| 5,561,983 A | * 10/1996 | Remes et al. | ................. 62/50.7 |
| 5,906,100 A | 5/1999 | Caldwell et al. | |
| D437,056 S | 1/2001 | Remes et al. | |

FOREIGN PATENT DOCUMENTS

| | | |
|---|---|---|
| GB | 1185199 | 3/1970 |
| WO | WO 98/58219 | 12/1998 |

* cited by examiner

*Primary Examiner*—Ronald Capossela
(74) *Attorney, Agent, or Firm*—Rothwell, Figg, Ernst & Manbeck

(57) ABSTRACT

A manifold for a liquid oxygen (LOX) storage/delivery apparatus is provided according to the invention. The manifold for a liquid oxygen (LOX) storage/delivery apparatus includes a gas conduit adapted to communicate with a source of gaseous oxygen, the gas conduit allowing passage of gaseous oxygen and containing a liquid oxygen conduit inside the gas conduit, with the liquid oxygen conduit passing through the manifold, a gas withdrawal conduit communicating with the gas conduit, and a gas vent conduit communicating with the gas conduit. The manifold permits independent liquid oxygen passage, independent gaseous oxygen passage, and independent gaseous oxygen venting.

11 Claims, 3 Drawing Sheets

MANIFOLD FOR USE IN A PORTABLE LIQUID OXYGEN UNIT

CROSS REFERENCE TO RELATED APPLICATION

The present application claims priority from U.S. Provisional patent application Serial No. 60/162,132, filed Oct. 29, 1999. The disclosure of the above-referenced provisional patent application is incorporated herein by reference in its entirety.

BACKGROUND OF THE INVENTION

1. Field of the Invention

The present invention relates generally to a liquid oxygen manifold, and more particularly to a manifold for use with a liquid oxygen storage/delivery apparatus.

2. Description of the Background Art

Therapeutic oxygen is the delivery of relatively pure oxygen to a patient in order to ease pulmonary/respiratory problems. When a patient suffers from breathing problems, inhalation of oxygen may ensure that the patient is getting an adequate level of oxygen into his or her bloodstream.

Therapeutic oxygen may be warranted in cases where a patient suffers from a loss of lung capacity for some reason. Some medical conditions that may make oxygen necessary are chronic obstructive pulmonary disease (COPD) including asthma, emphysema, lung cancer, etc., as well as cystic fibrosis, lung injuries, and cardiovascular diseases, for example.

Related art practice has been to provide portable oxygen in two ways. In a first approach, compressed oxygen gas is provided in a pressure bottle, and the gas is output through a pressure regulator through a hose to the nostrils of the patient. The bottle is often wheeled so that the patient may be mobile. This is a fairly simple portable arrangement.

The drawback of compressed, gaseous oxygen is that a full charge of a bottle that is portable does not last a desirable amount of time. In order to get around this limitation, in a second approach a related art liquid oxygen (LOX) apparatus has been used wherein liquid oxygen is stored in a container and the gaseous oxygen that evaporates from the LOX is inhaled by the patient.

The LOX apparatus enjoys a longer usable charge than the compressed gas apparatus for a given size and weight, but has its own drawbacks. LOX, being a liquid that is very cold, requires a vacuum-insulated container.

The LOX in a storage container transforms from a liquid state to a gaseous state as it warms, with a resultant increase in internal gas pressure. Therefore, a LOX storage container typically contains both liquid and gaseous phases of oxygen.

FIG. 1 shows a related art LOX storage container 100, having an inner container 104 and an outer container 107. The two are usually separated by at least a partial vacuum to reduce heat transfer to the LOX. For input and output ports, the inner container 104 is formed with a neck that is inside a similar neck formed in the outer container 107. Input and output ports may include a liquid withdrawal port 112, a gas withdrawal vent port 111, and a gas vent port 110. One of these ports may also be a liquid fill port, or a separate liquid fill port may exist on the related art LOX storage container 100. As a result, the related art storage container 100 may suffer from unacceptable levels of heat transfer via conduction by the necks of the various ports of the inner storage container 104.

Use of related art storage container typically requires a gas vent tube, a gas withdrawal tube, and a liquid withdrawal tube. The multiple ports require multiple transition joints, and multiple attachments such as welds, resulting in multiple heat entry points and a greater reliability concern.

There remains a need in the art, therefore, for an improved LOX storage/delivery apparatus.

SUMMARY OF THE INVENTION

A manifold for a liquid oxygen (LOX) storage/delivery apparatus is provided according to the invention. The manifold for a liquid oxygen (LOX) storage/delivery apparatus comprises a gas conduit adapted to communicate with a source of gaseous oxygen, the gas conduit allowing passage of gaseous oxygen and containing a liquid oxygen conduit inside the gas conduit, with the liquid oxygen conduit passing through the manifold, a gas withdrawal conduit communicating with the gas conduit, and a gas vent conduit communicating with the gas conduit, wherein the manifold permits independent liquid oxygen passage, independent gaseous oxygen passage, and independent gaseous oxygen venting.

The above and other features and advantages of the present invention will be further understood from the following description of the preferred embodiment thereof, taken in conjunction with the accompanying drawings.

DETAILED DESCRIPTION OF THE PREFERRED EMBODIMENTS

Figure 1:
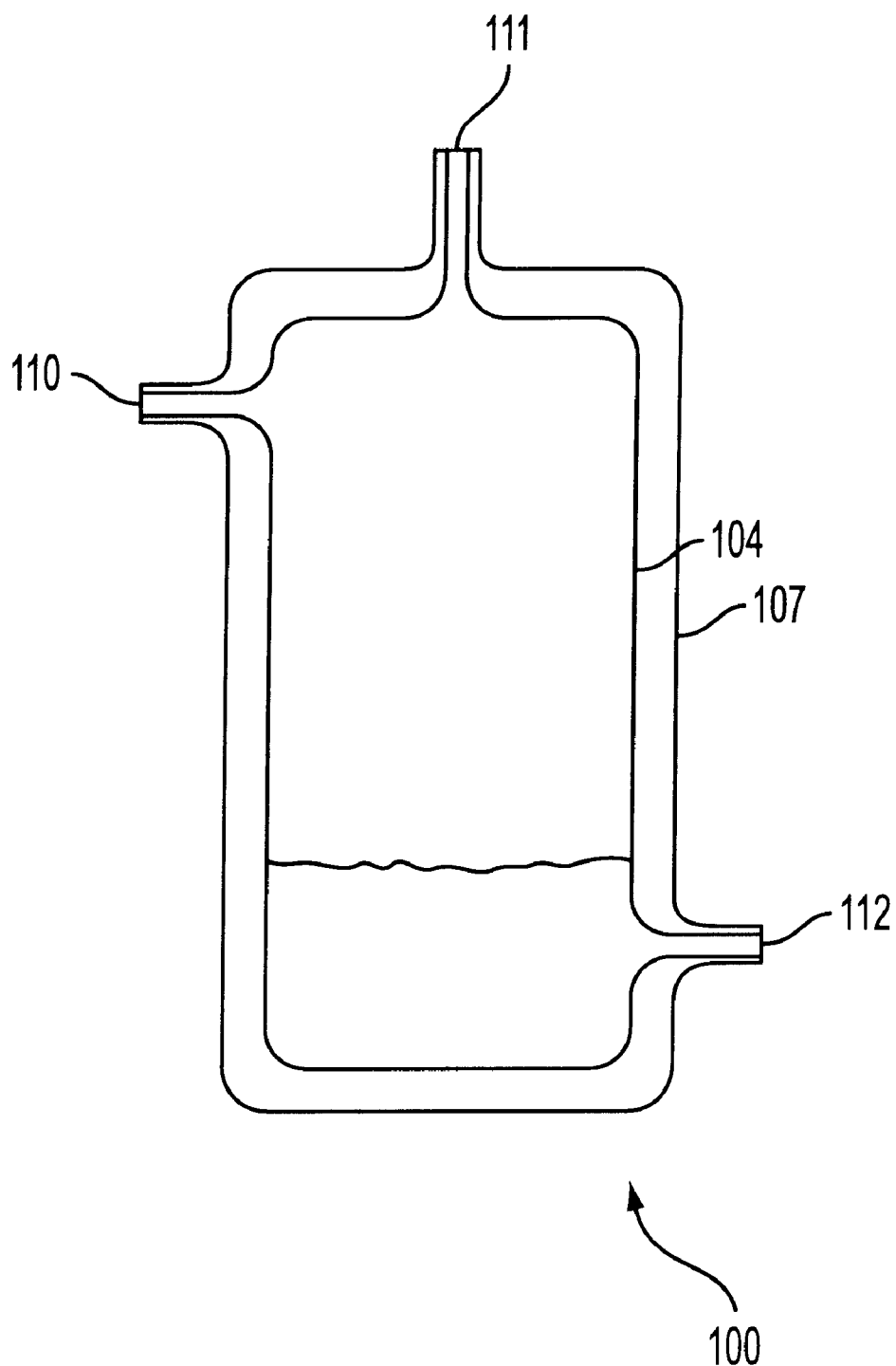
FIG. 1 schematically shows a related art LOX storage container having an inner container and an outer container.
Figure 2:
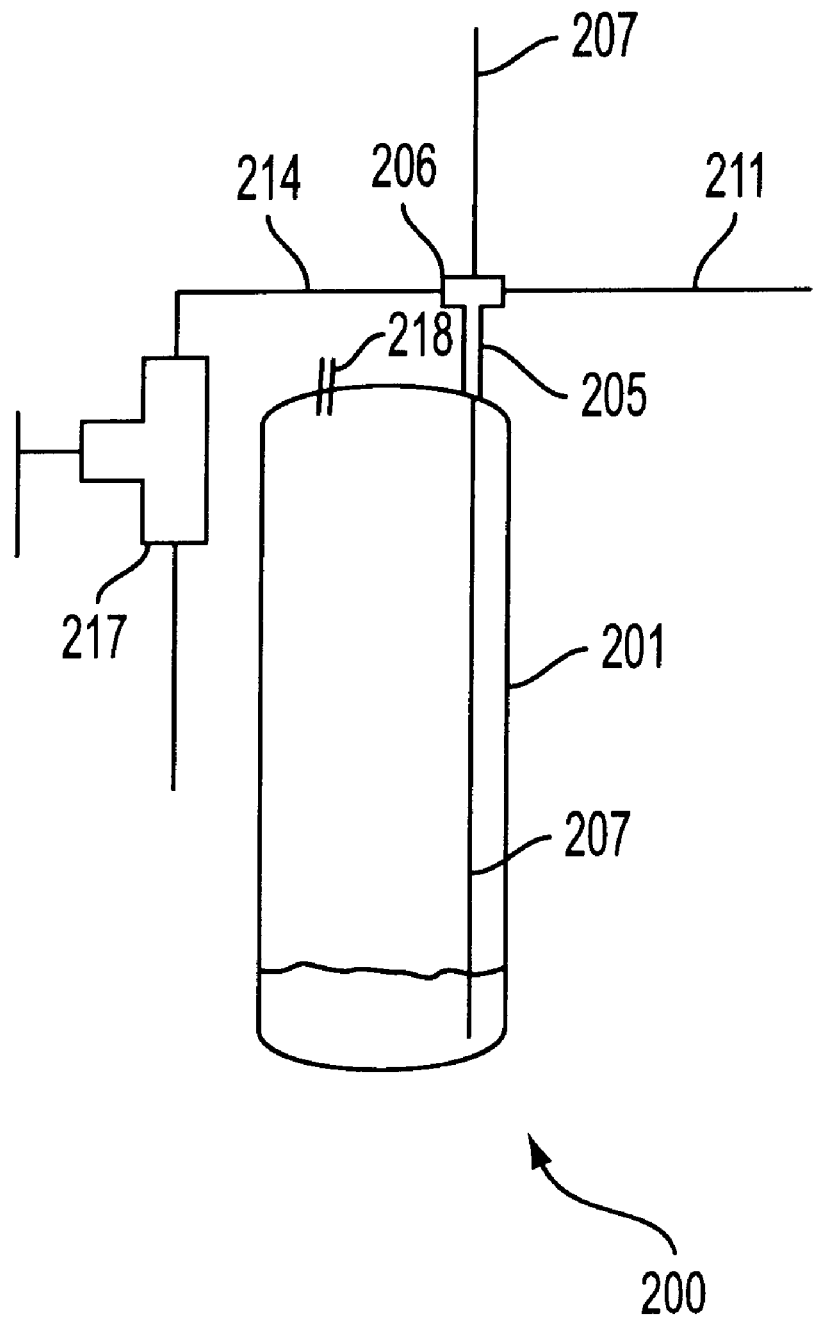
FIG. 2 schematically shows a LOX storage/delivery apparatus.

FIG. 2 shows a LOX storage/delivery apparatus 200. The LOX storage/delivery apparatus 200 includes a storage container 201 that may contain both liquid and gaseous oxygen, a manifold 206, a gas conduit 205, a gas vent conduit 214, a gas withdrawal conduit 211, and a liquid withdrawal conduit 207. In use, the apparatus 200 will normally employ a vent valve 217 attached to the gas vent conduit 214. Container 201 is charged with LOX through port 218 in communication with the interior of container 201.

Figure 3:
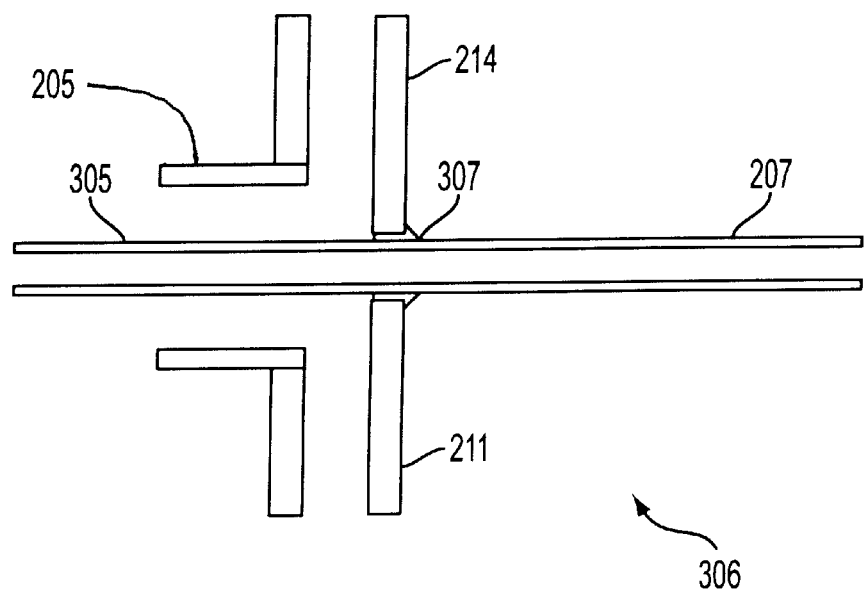
FIG. 3 schematically shows detail of a first embodiment of the manifold of the present invention.

FIG. 3 shows detail of a first embodiment 306 of the manifold of the present invention. It can be seen that the gas conduit 205 includes an internal liquid withdrawal conduit 305 inside the gas conduit 205. The internal liquid withdrawal conduit 305 may or may not be concentric with the gas conduit 205. The internal liquid withdrawal conduit 305 becomes the liquid withdrawal conduit 207 after exiting the manifold 306. At the point of exit, the liquid withdrawal tube 207 may include a weld 307. Preferably, the weld 307 may be a brazing type weld.

The manifold 306 allows simultaneous liquid withdrawal (through the liquid withdrawal conduit 207), gaseous oxygen withdrawal through the gas withdrawal conduit 214 (for consumption), and gaseous oxygen venting through the gas vent conduit 211. The gas withdrawal is done through the gas conduit 205 because the larger size (as compared to the internal liquid conduit 305) is preferred. The gas vent conduit 211 allows gaseous oxygen to exit as LOX enters the system.

Figure 4:
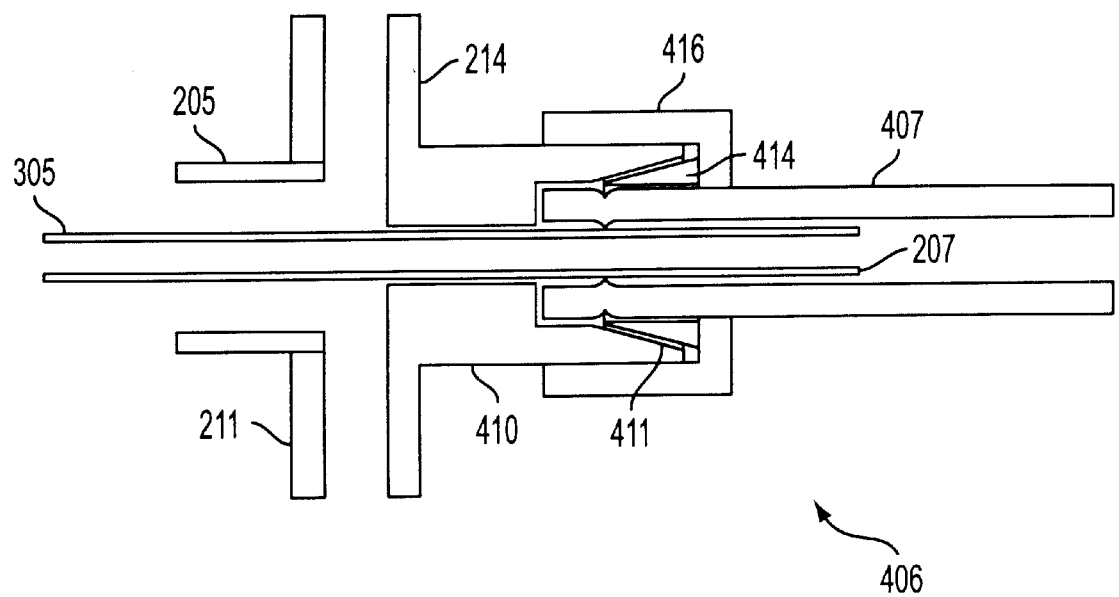
FIG. 4 schematically shows detail of a second embodiment of the manifold of the present invention.

FIG. 4 shows detail of a second embodiment 406 of the manifold of the present invention. In place of the weld 307, the manifold 406 includes an extended portion 410 having a beveled opening 411. The liquid withdrawal conduit 207 emerges from the beveled opening 411. A connecting conduit 407 is placed over and crimped onto the liquid withdrawal conduit 207, sealingly connecting the two. A ferrule ring 414 may be positioned over the connecting conduit 407 and within the beveled portion of the beveled opening 411. A fitting nut 416 is then placed over the connecting conduit 407 and after the ferrule ring. When the fitting nut is in a fastened position, such as, for example, by screwing said fitting nut 416 onto an exterior threaded surface of the extended portion 410 (not shown), the fitting nut 416 forces the ferrule ring 414 against the connecting conduit 407 and the beveled portion of the beveled opening 411. The fitting nut 416 and the ferrule ring 414 therefore sealingly hold the connecting conduit 407 in the manifold 406. The fitting nut 416 may also be attached to the extended portion 410 in other ways, such as, for example, a snap fit.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A manifold for a liquid oxygen (LOX) storage/delivery apparatus comprising:

a gas conduit adapted to communicate with a source of gaseous oxygen, said gas conduit allowing passage of gaseous oxygen and containing a liquid oxygen conduit inside said gas conduit, with said liquid oxygen conduit passing through said manifold;

a gas withdrawal conduit communicating with said gas conduit; and a gas vent conduit communicating with said gas conduit;

wherein said manifold permits independent liquid oxygen passage, independent gaseous oxygen passage, and independent gaseous oxygen venting.

2. The apparatus of claim 1 wherein said gas conduit is substantially concentric with said liquid oxygen conduit.

3. The manifold of claim 1, wherein said liquid oxygen conduit is welded into said manifold.

4. The manifold of claim 1, wherein said liquid oxygen conduit is brazed into said manifold.

5. The manifold of claim 1, wherein said gas vent conduit is positioned on one side of said manifold and said gas withdrawal conduit is located on substantially an opposite side of said manifold.

6. The manifold of claim 1, wherein gas conduit is located on a first side of said manifold, and said liquid oxygen conduit exits said manifold on a second side of said manifold substantially opposite said first side.

7. The manifold of claim 1, wherein said manifold further comprises:

an extended portion having an opening, with said opening including a beveled surface;

a fitting nut; and a ferrule ring;

wherein a connecting conduit is fitted over said liquid oxygen conduit where said liquid oxygen conduit exits said manifold at said opening, with said ferrule ring being placed over said connecting conduit and said fitting nut being placed over said connecting conduit, with said fitting nut in a fastened position forcing said ferrule ring against said connecting conduit and said beveled surface of said opening and sealingly holding said liquid oxygen conduit and said connecting conduit in said manifold.

8. The apparatus of claim 7, wherein said connecting conduit is sealingly crimped onto said liquid oxygen conduit.

9. A portable liquid oxygen (LOX) storage/delivery apparatus, comprising:

an insulated LOX container having an interior for containing LOX;

a port system in communication with said interior of said container, said port system comprising a manifold as defined in claim 1, wherein said gaseous oxygen is withdrawn from said container through a first outlet comprising an open end of said gas conduit communicating with a portion of the interior of said container for containing gaseous oxygen; and wherein LOX is withdrawn from said container through a second outlet comprising an open end of said liquid oxygen conduit communicating with a portion of the interior of said container for containing LOX.

10. The apparatus of claim 9 wherein said gas conduit is substantially concentric with said liquid oxygen conduit.

11. The apparatus of claim 9 wherein said container is charged with LOX through a third port in communication with the interior of said container.

* * * * *